United States Patent [19]
Roesicke

[11] Patent Number: 6,148,666
[45] Date of Patent: Nov. 21, 2000

[54] METHOD AND DEVICE FOR LIQUID TRANSFER WITH AN ANALYSIS APPARATUS

[75] Inventor: Bernd Roesicke, Mannheim, Germany

[73] Assignee: Boehringer Mannheim GmbH, Mannheim, Germany

[21] Appl. No.: 09/181,647

[22] Filed: Oct. 29, 1998

[30] Foreign Application Priority Data

Oct. 29, 1997 [DE] Germany ............................ 197 47 667
Dec. 19, 1997 [DE] Germany ............................ 197 56 842

[51] Int. Cl.[7] .............................. G01F 23/00; G01N 1/14; G01N 31/00; B01L 3/02
[52] U.S. Cl. .................. 73/290 R; 73/304 C; 73/304 R; 73/864.11; 73/61.63; 422/66; 422/67; 422/68.1; 340/620
[58] Field of Search .............................. 73/290 R, 61–63, 73/304 C, 304 R, 864.11; 422/67, 66, 68.1; 340/620

[56] References Cited

U.S. PATENT DOCUMENTS

| | | | |
|---|---|---|---|
| 3,754,444 | 8/1973 | Ure et al. | 73/423 |
| 4,338,279 | 7/1982 | Orimo et al. | 422/64 |
| 4,451,433 | 5/1984 | Yamashita et al. | 422/63 |
| 4,543,238 | 9/1985 | Mimura et al. | 422/63 |
| 4,635,478 | 1/1987 | Hope | 73/292 |
| 4,647,432 | 3/1987 | Wakatake | 422/64 |
| 4,736,638 | 4/1988 | Okawa et al. | |
| 4,818,492 | 4/1989 | Shimizu | |
| 4,939,925 | 7/1990 | Sakuma et al. | 73/61 |
| 5,004,582 | 4/1991 | Miyata et al. | 422/56 |
| 5,045,286 | 9/1991 | Kitajima et al. | 422/100 |
| 5,049,826 | 9/1991 | Sasao | 422/106 |
| 5,104,621 | 4/1992 | Pfost et al. | 422/67 |
| 5,147,610 | 9/1992 | Watanabe et al. | 422/64 |
| 5,178,019 | 1/1993 | Keiter | 73/863.11 |
| 5,178,835 | 1/1993 | Uekiisa et al. | 422/66 |
| 5,212,992 | 5/1993 | Calhoun | 73/864 |
| 5,304,347 | 4/1994 | Mann et al. | 422/67 |

FOREIGN PATENT DOCUMENTS

| | | |
|---|---|---|
| 0 164 679 | 12/1985 | European Pat. Off. . |
| 0 280 965 | 9/1988 | European Pat. Off. . |
| 0 355 791 | 2/1990 | European Pat. Off. . |
| 2 245 707A | 1/1992 | United Kingdom . |
| 2 245707 | 1/1992 | United Kingdom . |

*Primary Examiner*—Hezron Williams
*Assistant Examiner*—Dennis Loo
*Attorney, Agent, or Firm*—Arent Fox Kintner Plotkin & Kahn PLLC

[57] ABSTRACT

A liquid transfer device for an analysis unit includes a transfer needle having a tip, and a capacitive liquid level detector for detecting immersion of the tip of the needle into an analysis liquid by detecting a change in capacitance between a signal electrode and a counter electrode. The analysis liquid is contained in a vessel. The capacitive liquid level detector includes a signal electrode, a counter electrode, and a detection circuit connected to the signal electrode and the counter electrode. The detection circuit detects a change in capacitance between the signal electrode and the counter electrode. A temperature dependent detection resistor is disposed adjacent the tip of the liquid transfer needle. The tip of the liquid transfer needle and the temperature dependent detection resistor are movable into and out of the analysis liquid. The detection circuit includes a current supply for supplying current to the detection resistor. The detection circuit is configured to detect a change in resistance of the detection resistor during a immersion thereof into the analysis liquid.

18 Claims, 7 Drawing Sheets

METHOD AND DEVICE FOR LIQUID TRANSFER WITH AN ANALYSIS APPARATUS

BACKGROUND OF THE INVENTION

1. Field of the Invention

The invention concerns a liquid transfer device for an analysis apparatus having a liquid transfer needle and a capacitive liquid level detector for the detection of the dipping of the liquid transfer needle into an analysis liquid located in a vessel, wherein the liquid level detector has a signal electrode, a counter electrode and a detection circuit for the detection of a change in the capacitance between the signal electrode and the counter electrode. The invention also concerns an associated method for the detection of the dipping of the liquid transfer needle.

2. Description of Related Art

In analysis apparatus used for the analysis of body fluids, in particular of blood, liquid transfer devices are required in order to transfer analysis liquids, in particular liquid samples or reagents. Conventional liquid transfer devices include, for example, pipettes which are utilized to suction samples or reagents out of a first vessel and to expel them into a second vessel as well as dispensers with which the liquid transfer needle is connected by means of a tube to a large supply of liquid which can be discharged through the needle with the assistance of a pumping device. Dispensers generally also fulfill the function of a pipette.

In association with the present invention, the designation liquid transfer device generally refers to any device facilitating dipping into an analysis liquid in an analysis apparatus to effect any kind of liquid transfer operation (suctioning up and/or expulsion of liquid) using a liquid transfer needle. The liquid transfer needle is a hollow needle which normally consists essentially of a thin tube made from metal or plastic. For reasons of simplicity this is subsequently referred to as a "needle".

When the needle is immersed deeply into the analysis liquid, a relatively large excess amount of liquid remains on its outer side. This leads to a decrease in the precision of the dosage. In addition, this excess liquid can disadvantageously contaminate the liquid into which the needle is, subsequently submerged (so-called "carry-over").

In order to be able to better monitor the submersion depth, liquid transfer devices are provided with a sensing device for the detection of the dipping of the needle into the analysis fluid, usually designated liquid level detectors or LLD. The liquid level detector is connected to the vertical drive used to submerge the needle into the analysis liquid in order to stop the submersion motion when the tip of the needle has dipped a few millimeters into the analysis liquid. In addition to preventing carry-over, one must simultaneously assure that air is not suctioned in which could lead to measurement errors affecting the diagnosis. For this reason, a minimum submersion depth must be maintained, which can be approximately between 0.1 mm and 2 mm.

The vertical position of the needle simultaneously provides indication of the level of the liquid in the respective vessel. For this reason, the liquid level detector simultaneously facilitates monitoring of the amount of liquid in the respective vessel to issue a signal when the supply of a reagent liquid is used up and the reagent bottle must be exchanged.

A conventional principle of construction for the liquid level detector is based on the measurement of the electrical resistance between the needle and an electrode disposed on the needle tip. The needle and the electrode are electrically insulated with respect to each other so that the electrical resistance between them is very high in a dry state. When the needle and the electrode are submerged, the sample liquid provides a conductive connection so that the electrical resistance changes abruptly. This signal can be reliably detected using simple electronics. This method has the substantial disadvantage, however, that both the needle and an electrode must dip into the liquid, on which unavoidable amounts of excess liquid necessarily remain. The above mentioned problem with respect to carry-over and associated reduced precision is thereby exacerbated.

In this regard, capacitive liquid level detectors are superior. The detection signal for dipping of the needle into the liquid is thereby given by the change in the electrical capacitance between two sensor electrodes via an electronic detection circuit including an alternating voltage source. The first electrode is thereby normally the needle itself,(which is made from metal or from an electrically conducting (metallized) plastic) and is connected to the hot terminal of the alternating voltage source (signal electrode). The counter electrode, which is usually at ground, is disposed on the outer side of the liquid container of the conventional devices (beneath its bottom and partially around the side walls of the container). This electrode is normally part of the container support. When the needle tip enters into the liquid, the capacitance between the signal electrode and the counter electrode changes due to the electrical conductivity and dielectric properties of the liquid.

These types of liquid level detectors are described in EP-A-0 164 679, U.S. Pat. No. 4,818,492 and EP-A-0 355 791. These publications contain more detailed descriptions, the complete disclosure of which are hereby incorporated by reference.

A fundamental problem of capacitive liquid level detectors is that the change in capacitance when entering into the fluid is very small compared to other unavoidable capacitances ("interfering capacitances") or stray capacitances, such as the connecting cable and the input of the amplifier). The ratio between the useful signal and the interfering signal is therefore poor. A particular problem thereby is that a portion of the interfering capacitance is not constant, but can change as a function of time in a relatively rapid manner. This is particularly true for capacitive interference caused by moving objects (parts of the automated analysis system, hands or other body parts of the person using the apparatus). Particularly in fully automatic analysis apparatuses having a plurality of moving components, such interferences are, in practice, unavoidable.

EP-A-0 355 791 addresses a particular problem of this kind (interference by a membrane closing the container) by setting a reference signal when the membranes contacts and, during the subsequent downward motion of the needle, detecting the difference relative to this fixed referencesignal. This method is directed to the particular application. Interfering capacitances which change between the fixing of the reference signal and the detection of the liquid surface lead to errors in detection.

The liquid level detector described in U.S. Pat. No. 4,818,492 passively compensates for the interfering capacitances of the leads with the assistance of a bridge circuit. Other capacitive interferences are not thereby eliminated, however, and could also lead to improper detection in this particular configuration.

A liquid transfer device for an analysis apparatus having a liquid level detector with improved resistance to interference and more reliable operation is known in the art from U.S. Pat. No. 5,304,374, which is hereby incorporated by reference. This publication proposes a coaxial electrode configuration including the liquid transfer needle and having an active shield via a compensation electrode connected to a voltage follower circuit. In addition, in an advantageous improvement thereof, an additional shielding electrode functions as a counter electrode at constant potential.

Such a coaxial, in particular triaxial configuration having an active shielding and accompanying reference electrode facilitates, without specific adjustment or adaptation and independent of the constructive details of the surrounding apparatus, the filling amounts and the dielectric properties of the liquid, the detection of the liquid level on all positions in the apparatus which can be reached by the needle. This is true substantially since the signal path leads from the needle tip, capacitively, to the surface of the liquid and from this location along a conceptual electric conductance along the surface of the liquid and subsequently via a capacitive signal path back to the accompanying reference electrode so that the lower portions of the liquid column have negligible effects. The liquid level detector therefore reacts extremely sensitively to capacitive changes in the vicinity of the tip so that environmental influences do not falsify detection to as great an extent.

It has, however, turned out that the extreme sensitivity in the vicinity of the tip of the liquid transfer needle can also be disadvantageous, since all moist films in the vicinity of the tip are detected as a surface of a compact, firm fluid even when the tip of the needle has not yet reached the actual surface of the liquid. In order to avoid this, special complicated error correction strategies can be developed and applied, such as subsequent displacement, plurality of insertions, pressure measurements or plausibility checks at predictable fill levels.

In particular, a formation of foam or soap-bubble-like structures can constitute liquid films which can falsify detection of the liquid surface. These structures are relatively long-lived and cannot necessarily be destroyed by penetration of the liquid transfer needle. Such foam layers or soap-bubble-like structures occur, e.g. when shaking a thoroughbred sample, during centrifuge operation of blood samples for the extraction of serum plasma, during transport of reagent rack-packs and by the resuspending and stirring of so-called beads coated with streptavidin. These types of foam layers are normally 2 to 5 mm thick. Bubbles formed on the collar of the vessel are also not popped in many cases by the thin liquid transfer needle.

SUMMARY OF THE INVENTION

It is therefore the underlying purpose of the invention to improve conventional capacitive liquid level detectors, in particular those disclosed in U.S. Pat. No. 5,304,347 having a triaxial configuration with an actively shielded compensation electrode and accompanying shielding electrode functioning as a counter electrode, in such a fashion that error free differentiation between compact dense liquid and foam or liquid films can be achieved.

This purpose is achieved with a liquid transfer device of the above mentioned kind having a capacitive liquid level detector in that the liquid level detector also comprises a temperature dependent detection resistor which is disposed in the vicinity of the liquid transfer needle tip and which can be submerged along therewith into the analysis liquid. The detection circuit thereby comprises a current supply to supply current to the detection resistor and is adapted for the detection of a change in resistance of the detection resistor during submersion into the analysis liquid.

The fundamental idea underlying the invention is the detection of the dipping of the liquid transfer needle into the analysis liquid with the additional measurement of the change in resistance of a temperature dependent detection resistor disposed in the vicinity of the tip of the liquid transfer needle and submerged along with the liquid transfer needle into the analysis liquid and through which current is flowing from a current supply. The detection resistor can thereby be used to check and verify a dipping into a fluid recognized by a capacitive liquid level detector.

A temperature dependent resistor, i.e. an NTC or a PTC, is located on, the tip of the liquid transfer needle or in the vicinity of the tip and has a very small and preferentially constant current flowing there through. When the tip of the liquid transfer needle and of the detection resistor is in air, the detection resistor warms slightly relative to the surrounding air. When the detection resistor is dipped into a foam or a bubble, only a small amount of heat transfer occurs through contact with the small amount of fluid constituting the bubble so that the temperature and thereby the detection resistance does not change or changes only slightly.

In contrast thereto, when the detection resistor dives into a compact dense liquid, a substantially greater amount of heat is transferred so that a noticeable abrupt temperature change and thereby a resistance change occurs which can be detected through measurement techniques. This additional signal from the detection resistor can therefore be used to differentiate between thin liquid films or foam bubbles and a compact liquid so that the submersion into the analysis liquid can be uniquely detected.

The invention is based on the fact that the temperature of the detection resistor and thereby its resistance is significantly different when submerged into the liquid than the temperature and resistance in air or in a thin liquid film or foam bubble. Submersion into the liquid can therefore lead not only to a decrease in temperature of the detection resistor but also to a detectable increase in temperature, e.g. with incubation rotors.

One should however thereby take into account that the detection resistor is dimensioned and its operating conditions adjusted in such a fashion that a warming of the analysis liquid coming in contact therewith does not lead to a destructive change or influence in the properties of the analysis liquid. For thermally sensitive analysis liquids, it is advantageous when the temperature of the detection resistor does not exceed 37° C. A particular embodiment can thereby regulate the temperature of the detection resistor automatically relative to the surrounding temperature or to the temperature of the analysis liquid, in particular, to a fixed temperature difference exceeding or falling below the surrounding temperature. In general, sufficient detectable differences are associated with temperature changes in the detection resistor during submersion of between 1 K and 10 K, preferentially between 3K and 7K.

In principle, even a temperature dependent detection resistor alone, i.e. not in combination with a capacitive liquid level detector, could be used for the detection of submersion into the analysis liquid. However, such a construction is too slow for most applications to satisfy the demands on detection speed. The combination in accordance with the invention of a quickly responding capacitive liquid level detector along with a slower check by means of a detection resistor combines the advantages of both detection possibilities.

The added use of a detection resistor in accordance with the invention combined with thecapacitive liquid level detector is, in principle advantageous with all capacitive liquid level detectors independent of whether or not the capacitance of the liquid transfer needle is measured relative to ground or whether the liquid transfer needle is part of a coaxial electrode configuration. In general, checking with a detection resistor is always advantageous if the capacitive liquid level detector is configured in such a fashion that it is extremely sensitive to capacitive changes from its surroundings (sample, rotor, reagent vessel, static charges and the like) and, in particular, when it is extremely sensitive to capacitive changes around the tip of the liquid transfer needle. In contrast thereto, the detection resistor will not have substantial practical advantages if the mass of the detected fluid itself is incorporated into the signal path since, because in this case, the foam or bubble formation does not substantially affect detection of the liquid surface.

The invention is therefore preferred with coaxial electrode configurations in accordance with U.S. Pat. No. 5,304,347. Such coaxial electrode configurations advantageously have active shielding via a compensation electrode connected to a voltage follower circuit and/or a shielding electrode functioning as a counter electrode and extending into the region of the tip of the liquid transfer needle.

It is advantageous when the liquid transfer needle is part of a coaxial electrode configuration which, in addition to the liquid transfer needle, has at least one coaxial electrode surrounding same and insulated therefrom. It is also advantageous when the coaxial electrode configuration has a shielding electrode surrounding the signal electrode, wherein the shielding electrode is at constant potential and acts as a counter electrode.

It is also advantageous when the detection circuit has an alternating voltage source and a voltage follower circuit and when the input and output of the voltage follower circuit are connected to the neighboring electrodes of the coaxial electrode configuration constituting signal electrode and compensation electrode so that there is no voltage difference between the signal electrode and the compensation electrode to compensate for the capacitance between a signal electrode and a compensation electrode. In accordance with an additional advantageous feature, a first electrode of the coaxial electrode configuration is the signal electrode of the liquid level detector and is connected to the input of the voltage follower circuit and a second electrode of the coaxial electrode configuration, neighboring the signal electrode, is connected to the output of the voltage follower circuit.

It is also advantageous when the liquid transfer needle is connected, as a signal electrode, to the input of the voltage follower circuit and the neighboring coaxial electrode, as a compensation electrode, to the output of the voltage follower circuit.

BRIEF DESCRIPTION OF THE DRAWINGS

The invention is further described below with reference to embodiments schematically shown in the figures.

DETAILED DESCRIPTION OF THE PREFERRED EMBODIMENTS

Figure 1:
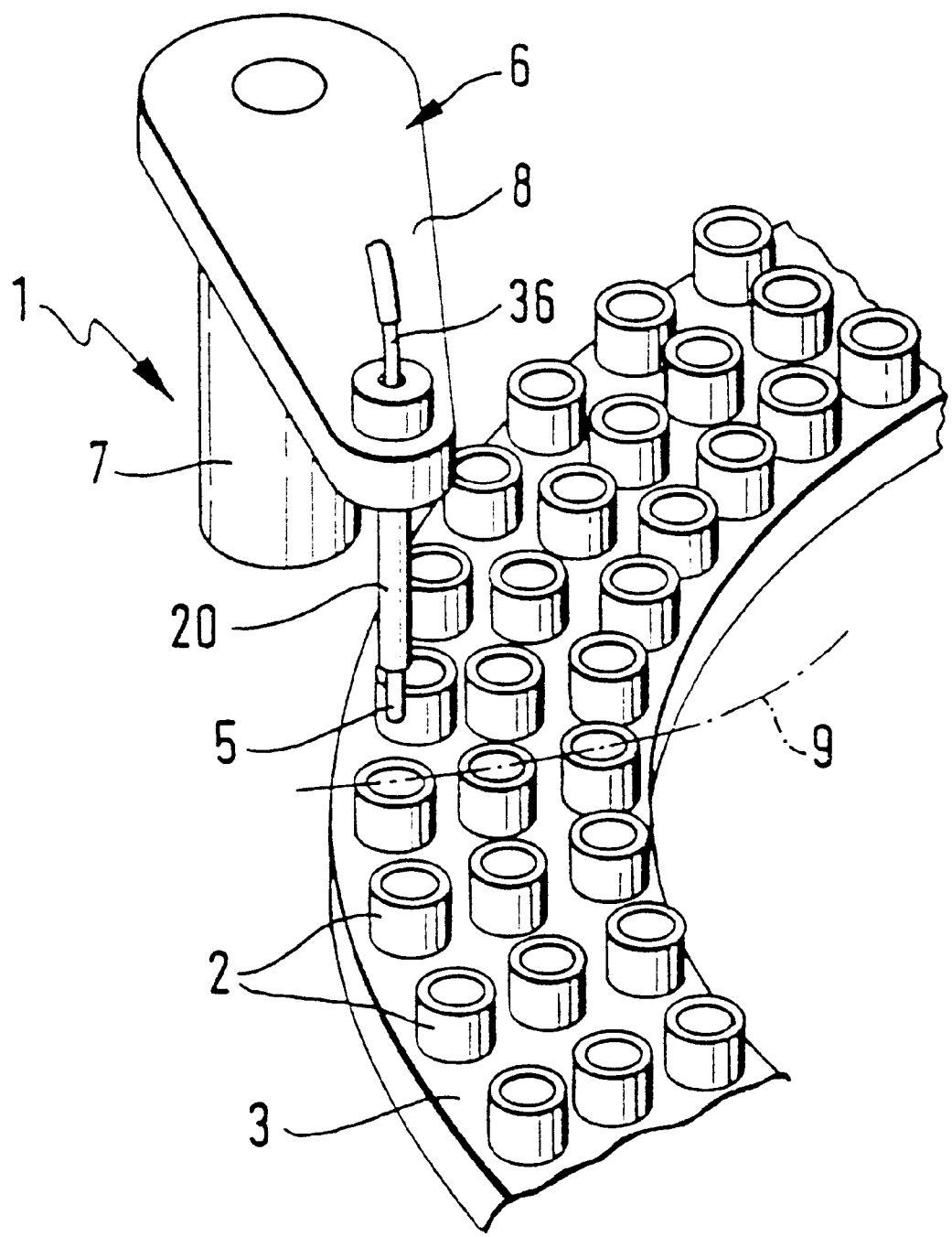
FIG. 1 shows a liquid transfer device in perspective view.

The liquid transfer device 1 shown in FIG. 1 removes an analysis liquid from one of the vessels 2 and transfers it into another vessel. The vessels 2 are located on a rotor 3 or another kind of movable vessel support. In practice, automatic analysis apparatuses normally comprise a plurality of vessel supports. The vessel volumes assume values of approximately 400 $\mu$l to 40 ml and the transferred fluid amount approximately 10–100 $\mu$l, with a resolution of approximately 0.25 $\mu$l. For incubation at 37° C., the liquids are dispensed in micro-cuvettes on an incubation rotor and the fill level must also be determined thereby.

A liquid transfer needle 5, having an inner diameter of approximately 0.4 mm, is mounted to a needle transport device 6 having a vertical column 7, which can be moved up and down by means of a vertical drive (not shown), as well as a pivoting arm 8. In this manner, the needle 5 can be positioned along the pivot circle 9 at various locations and lowered into one of the vessels 2. Such liquid transfer devices are known in the art in various embodiments. Reference is made to EP-A-0 408 804 with regard to a suitable drive mechanism.

Figure 2:
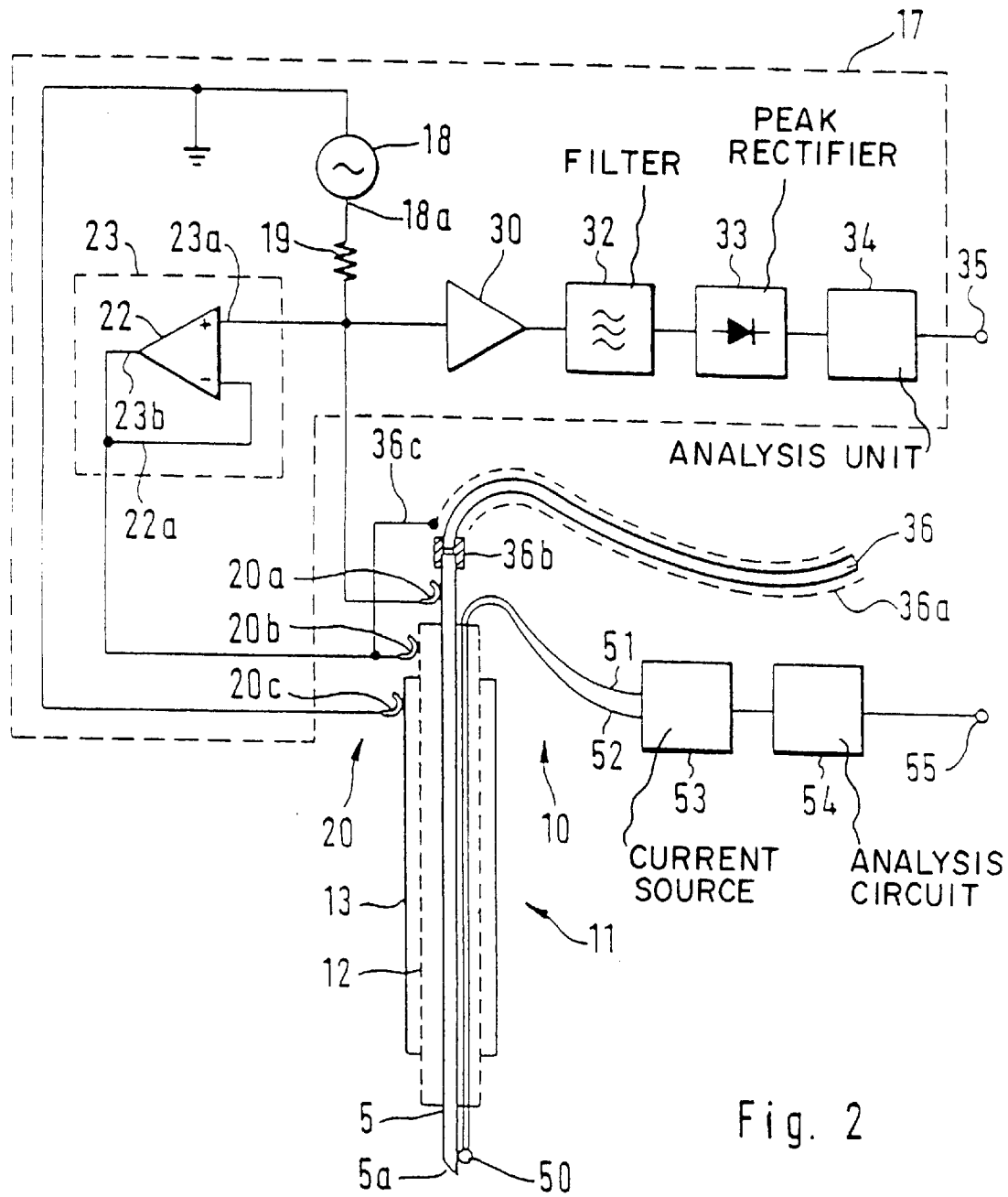
FIG. 2 shows a highly schematic cut representation through a coaxial electrode configuration combined with a schematic diagram of the detection circuit.
Figure 3:
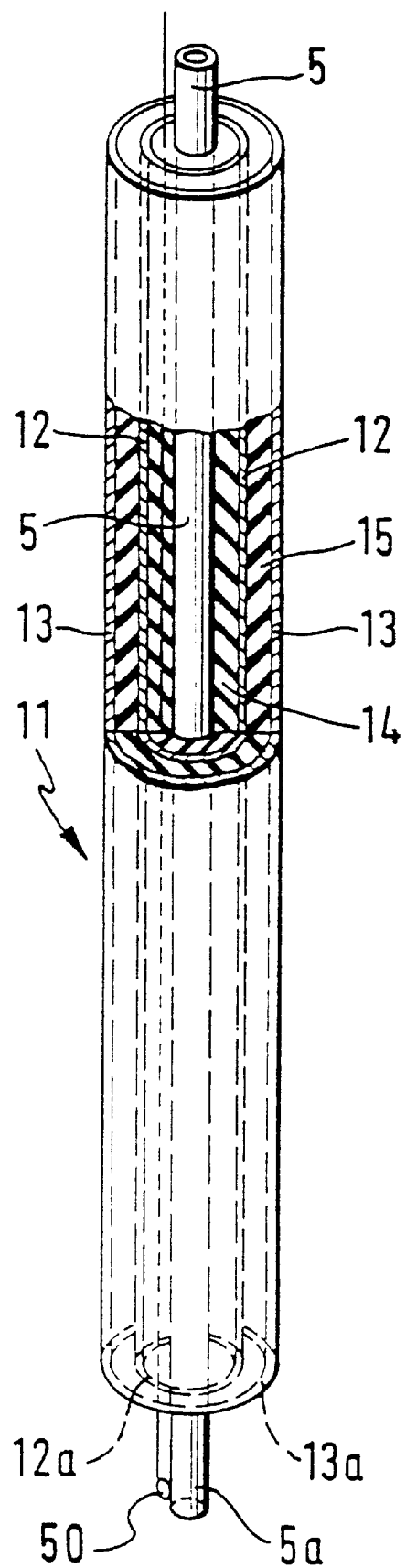
FIG. 3 shows a partially cut-open perspective view of a coaxial electrode configuration.

The liquid transfer needle 5 is preferentially part of a coaxial electrode configuration 11 shown in a highly schematic cross-sectional view in FIG. 2 and in a perspective manner in FIG. 3.

The liquid transfer needle 5, in a preferred embodiment, constitutes the innermost electrode of the coaxial electrode configuration 11 of a liquid level detector designated in its entirety with symbol 10. Reference is made to U.S. Pat. No. 5,304,347 with regard to details concerning the coaxial electrode configuration 11 shown, the electronic circuits, the advantages and possible alternative variations. The coaxial electrode configuration 11 includes the liquid transfer needle 5, a coaxial electrode 12 functioning as a compensation electrode for an active shielding, and a shielding counter electrode 13.

The liquid transfer needle 5 is completely surrounded in the radial direction about its entire perimeter by the compensation electrode 12 and the shielding electrode 13 and is fixed in space relative to these electrodes. The coaxial electrode 5 is thereby a fixed part of a coaxial electrode configuration 11 extending in the axial direction along a substantial length of the liquid transfer needle 5 with the exception of the needle tip 5a so that no relative motion occurs between the liquid transfer needle 5 and the surrounding electrodes. The compensation electrode 12 and the shielding electrode 13 are moved upwardly and downwardly along with the liquid transfer needle 5 by means of a needle transport device or, conversely, the vessel is lifted and lowered along with the analysis liquid in the direction towards the liquid transfer needle.

Due to the active shielding via the compensation electrode 12, the liquid transfer needle 5, serving as a signal electrode, is largely shielded during this relative motion between the liquid transfer needle 5 and the analysis liquid so that not the entire needle length is capacitively coupled to all conducting components in its surroundings, rather substantially only the unshielded tip of the needle 5a located at the lower end protruding out by a small amount. Therefore, the capacitance or the change in the capacitance is only detected at a location where it is useful for capacitive liquid level detection.

The capacitive detection circuit 17 includes an alternating voltage source 18 having a hot terminal 18a and a working resistor 19. The coaxial contact 20 to the coaxial electrode configuration 11 includes the connection to the innermost conductor 20a, to the first shield 20b, and to the second shield 20c. The liquid transfer needle 5 signal is fed to the non-inverted input 23a of the voltage follower circuit 23, which includes operational amplifier 22. The output 23b is coupled back via lead 22a to the inverted input and is also applied for active shielding to the compensation electrode 12. The detection circuit 17 further includes an amplifier 30, a filter 32, a peak rectifier or integrator 33 and an analysis unit 34 having output 35.

The tube 36 having the shielding 36a is connected via a tube connection 36b to the liquid transfer needle 5, wherein the shielding 36a is connected to the output 23b of the voltage follower circuit 23 and to the compensation electrode 12 via the connecting lead 36c.

In accordance with the invention, the coaxial electrode configuration 11 has a temperature dependent detection resistor 50 disposed in the vicinity of the tip 5a of the liquid transfer needle 5 and connected to a current supply 53 via two leads 51, 52. The current supply 53 is connected to an analysis circuit 54. An analog or digital signal is present on the output 55 of the analysis circuit 54 to indicate whether the detection resistor 50 is submerged in the analysis liquid 4 or is located in air or in foam 56 above the analysis liquid 4.

The detection resistor 50 is connected to the current supply 53 and the analysis circuit 54 in a two pole measurement technique, since extremely precise measurements of the detector resistor 50 resistance are not needed. For special applications, a four pole measurement could be carried out. The detection resistor 50 can be supplied with DC or AC current. When an AC voltage source is used, it is advantageous when its frequency is different from that of the capacitive liquid level detection. It is advantageous to utilize one of the electrodes 5, 12, 13 of the coaxial electrode configuration 11, in particular the liquid transfer needle 5, as a lead to the detection resistor 50 to thereby avoid additional leads and associated capacitive interference. The signals of the capacitive liquid level detector and the measurements of the resistance of the detector resistor 50 can thereby be separated through suitable modulation or filtering techniques.

Figure 4:
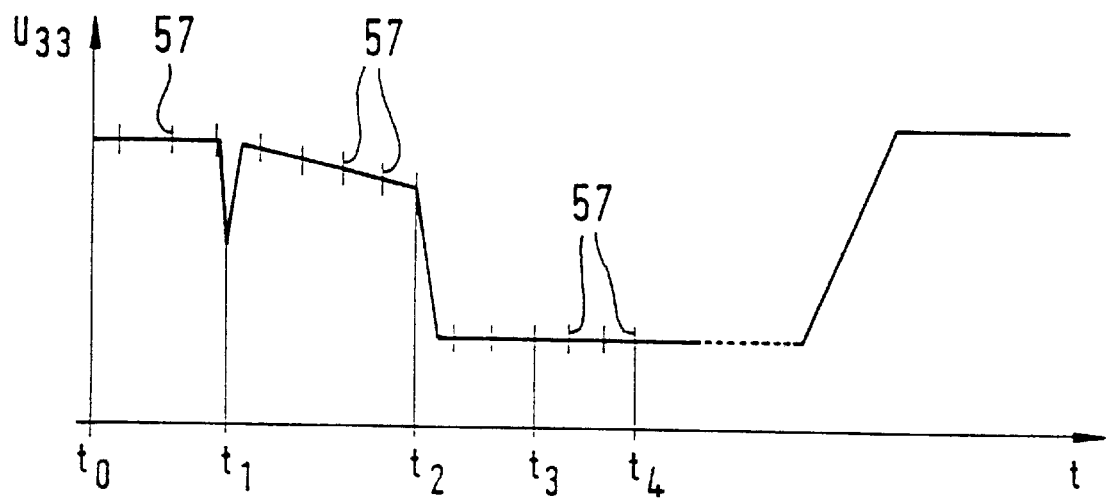
FIG. 4 shows a time diagram of a capacitive liquid level detector.

FIG. 4 shows a time diagram of the voltage $U_{33}$ at the output of the integrator 33 when the liquid transfer needle 5 is lowered towards the analysis liquid 4. The tip 5a is located, at time t=0, at a separation from the surface of the analysis liquid 4. The lowering motion is incrementally effected, wherein the transport velocity of the needle is approximately 1000 steps per second with a step size of 0.2 mm. It is thereby queried in regular time intervals of 1msec whether or not the voltage $U_{33}$ has changed with a certain speed. The sampling time points 57 are indicated by vertical dashes.

An interference occurs at time $t_1$ leading to a rapid transient reduction in the signal. Such an interference can e.g. be caused by electrostatic interference or by a popping bubble. The lowering motion of the liquid transfer needle 5 is, however, not stopped by the transient rapid sinking of the signal. Rather, subsequent to this event, one inquires a number of times, for example 3 times, whether or not a particular value remains below the last measured reference value prior to the interference. If this is not the case, e.g. since the bubble has broken in the meantime so that the tip 5a is therefore once more located in air, the lowering motion is continued, since one has recognized that the tip 5a has not yet dived into the analysis liquid 4.

At time $t_2$, the signal once more decreases rapidly and remains at this low level during the plurality of subsequent samplings 57. This indicates that the tip 5a has either dived into the analysis liquid 4 or that it is located in a bubble or in foam above the analysis liquid 4 which did not withdraw during insertion of the tip 5a. This decision, which must be taken within the shortest time possible in order to prevent excessive diving of the liquid transfer needle 5 into the analysis fluid 4, cannot be made using the signal from the capacitive liquid level detector 10 alone. Even e.g. if the sinking motion is stopped following 3 or 4 additional inquiry intervals and the possible decision conditions are fulfilled (i.e. a steep sinking of the signal is recognized by means of differentiation of the signal and triggering to a particular threshold value, comparison to a reference value prior to the trigger signal, and integration over a plurality of samplings to suppress interferences), it is nevertheless not possible to decide whether or not the tip 5a has actually dived into a dense fluid.

Figure 5:
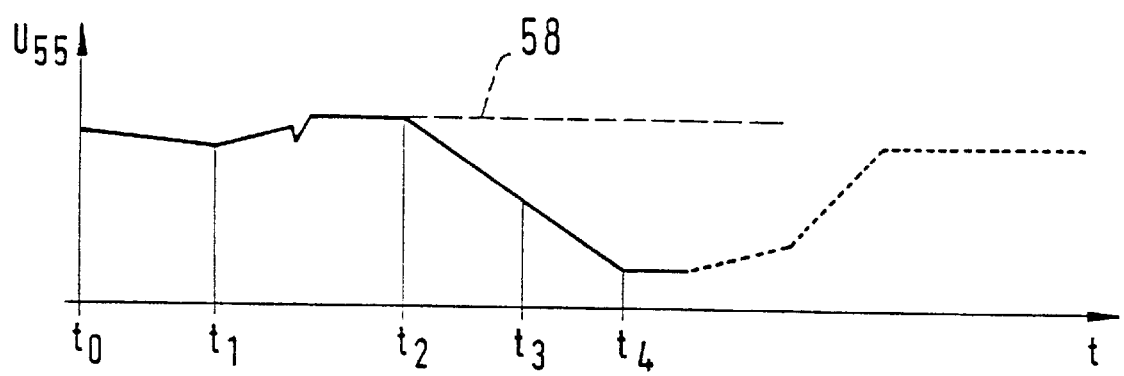
FIG. 5 shows a time diagram of a detection resistor.

In order to solve this problem, the voltage $U_{55}$ on the output 55 of the detection resistor 50 analysis circuit 54 is incorporated as a measure of the resistance of the detection resistor 50, the associated time dependence of which is shown in FIG. 5. The interference at time $t_1$ is not sensed by the detection resistor 50, since it is too slow.

The response time of the capacitive liquid level detector is approximately 1 ms or less, whereas the response time of the thermal measurement using the temperature dependent detection resistor 50 is approximately 10 to 100 ms. The rapid capacitive measurement for detection of changes along with the subsequent plausibility check by means of a slower thermal measurement in accordance with the invention results in an optimization between reaction time, i.e. minimal carryover, and the suppression of interferences, i.e. the reliable recognition of artifacts.

FIG. 5 shows that, at time $t_2$ the voltage $U_{55}$, indicating the temperature of the detection resistor 50, decreases. This can only happen when the detection resistor 50 is actually submerged in the analysis liquid 4. In the event of an interference, e.g. a non-exploded bubble, the signal would have the dashed alternative dependence 58. Measurement of the resistance of the detection resistor 50 at time $t_4$ can therefore be used to differentiate as to whether the liquid transfer needle 5, the downward motion of which has e.g. been stopped at time $t_3$, has actually dived into the analysis liquid 4 or not so that liquid transfer can be started or a new lowering initiated.

A variation thereof, which is particularly interesting for time critical applications in which a very quick measurement is required so that there is no time for subsequent checking using a temperature dependent detection resistor 50 prior to liquid transfer, provides for already initiating liquid transfer following stopping of the diving motion, i.e. at time period $t_3$ at which the capacitive checks have been completed. The detection resistor 50 measurement is carried out during liquid transfer. If the resistance measurement shows that the liquid transfer needle 5 has not yet been submerged into the analysis liquid at time period $t_3$ this is signaled to the analysis system and the measurement result of the current sample is retroactively discarded. In this manner, a higher throughput can be achieved.

Figure 6:
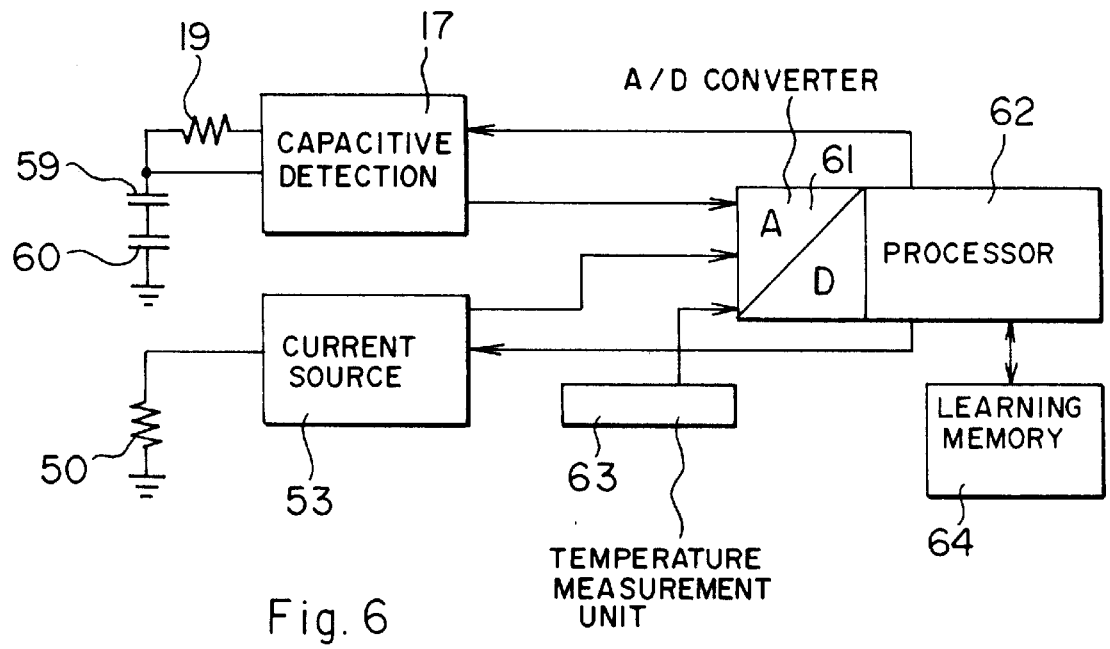
FIG. 6 shows a block circuit diagram of a first embodiment.

FIG. 6 shows a block diagram of a first embodiment. The detection circuit 17 includes an alternating voltage source, an impedance converter, a filter and a peak rectifier and analyzes the signal from the liquid level detector via a working resistor 19. The signal capacitances 59 between the shielding electrode 13 and the analysis liquid 4 as well as the capacitances 60 between the liquid 4 and the liquid transfer needle 5 are shown. The detection resistor 50 is supplied with current via a current supply 53. An analog to digital converter 61 reads out the data and a processor 62 controls the measurement.

The detection resistor 50 is heated up relative to the surrounding temperature, measured by a temperature measuring unit 63, via a small constant current. The measurement of the surrounding temperature or alternatively of the temperature of the analysis liquid 4 can be used to optimize the liquid transfer device to the actual operating conditions. The warming of the detection resistor 50 should not affect any chemical or biological processes in the analysis liquid 4. A warming between 1K and 10K, preferentially between 3K and 7K, is normally sufficient. With incubated liquid at 37° C., the prewarming temperature of the detection resistor 50 in air can advantageously lie between room temperature and the incubation temperature.

A learning memory 64 is connected to the processor 62 in which the typical change behavior of the detection resistor 50 for submersion in foam, bubbles, liquids or its behavior during drafts and the like can be stored with the assistance of self-programming software structures of the control system in a design typical fashion or can be individually determined and stored for an apparatus.

The arrangement of the detection resistor 50 should be of low capacitance to avoid interfering of the capacitive liquid level detector 10 by means of stray capacitances. An advantageous embodiment thereby proposes disposing the detection resistor 50, or at least a lead, between the shield electrode 13 and a compensation electrode 12. The capacitive influences are thereby minimized, since the capacitance between the shield electrode 13 and the compensation electrode 12 is compensated by the voltage follower circuit 23.

Figure 7:
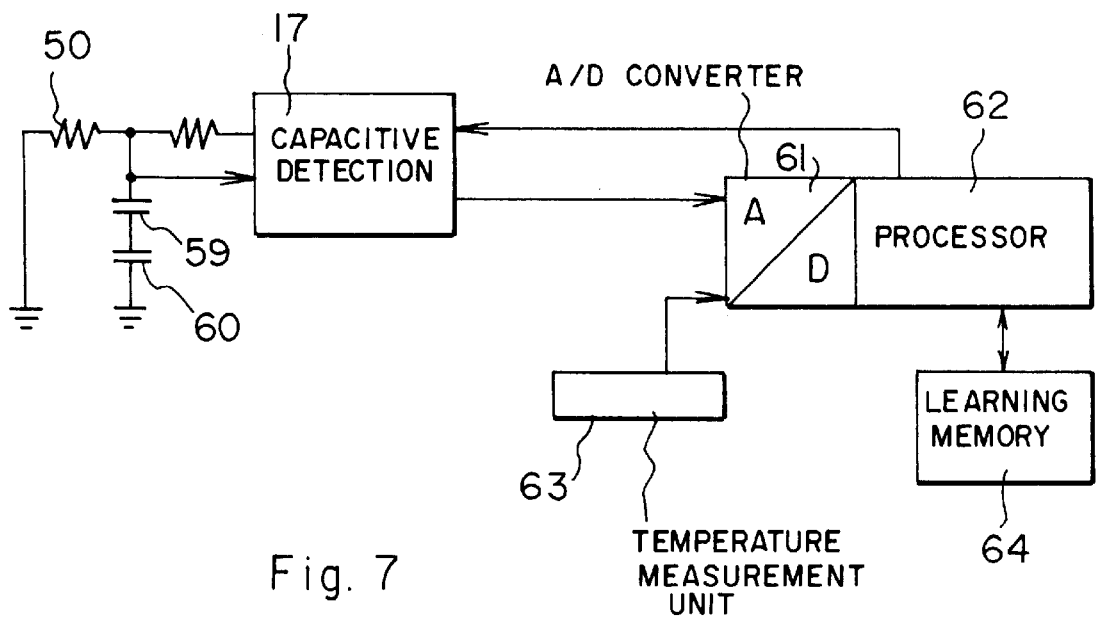
FIG. 7 shows a block circuit diagram of a second embodiment.

FIG. 7 shows another embodiment in which the detection resistor 50 is connected between the signal electrode 5 and a shield electrode 13. The detection resistor 50 is thereby supplied by the alternating voltage source 18 so that the capacitively detected signal has a parallel capacitive load. This can be advantageous if the capacitance of the detection resistor 50, including its connectors, is not significantly more than the signal capacitance. The output signal of the integrator 33 is then a combined signal from the capacitive portion of the capacitive liquid level detector 10 and a thermal component from the temperature dependent detection resistor 50, wherein the respective signal portions are determined by the processor 62. This configuration has the advantage that no separate leads are required to the detection resistor 50, since the electrodes, e.g. the liquid transfer needle 5, the shield electrode 13 or the coaxial electrode 12, can be used as leads. This configuration has, however, the disadvantage of an additional capacitive load to the capacitive signal path and the higher alternating current power which must be provided by the alternating voltage source 18.

Figure 8:
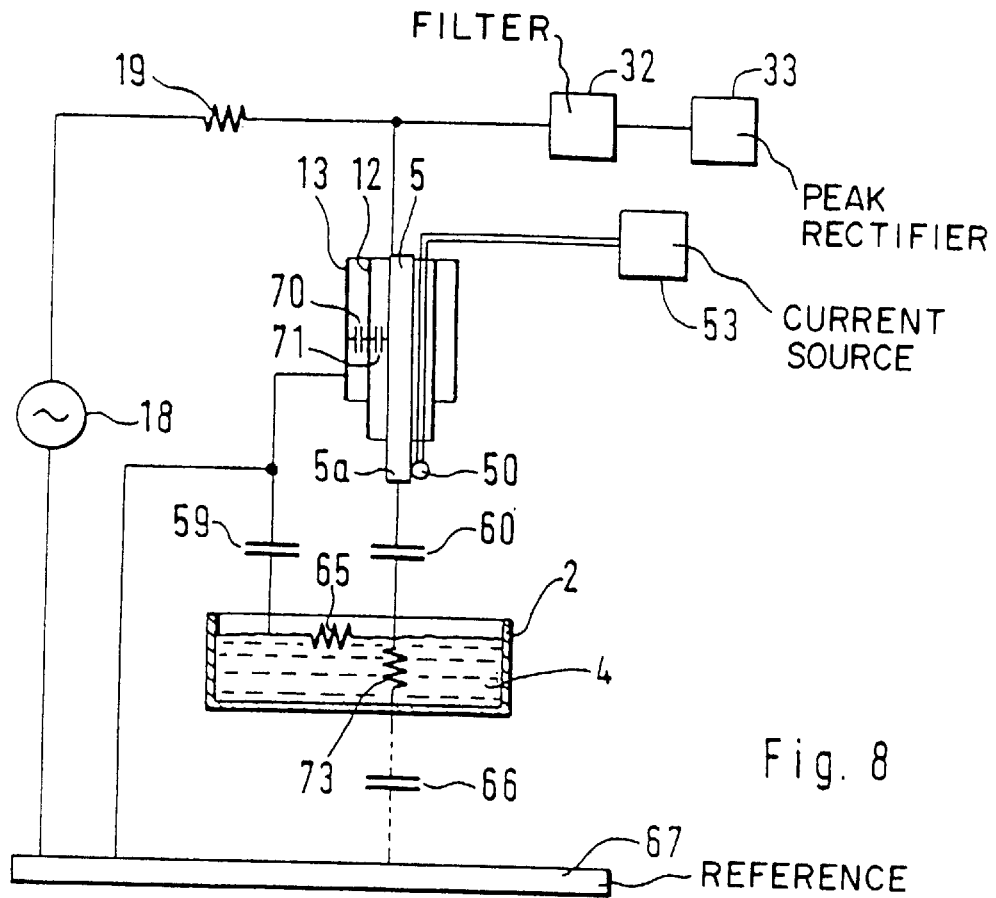
FIG. 8 shows a schematic representation of a detection circuit in accordance with the invention.

FIG. 8 illustrates the simplified capacitive relationships. The surface resistance 65 of the analysis liquid 4 lies between the two capacitances 59, 60. The capacitance 66 of the analysis liquid 4 (shown as dashed lines) with respect to the reference potential 67 can be neglected in the triaxial configuration. 73 designates the volume resistance of the analysis liquid 4. The capacitances 70, 71 which are large relative to the capacitances 59 and 60, are eliminated in this configuration by means of the identical potential on the liquid transfer needle 5 and the coaxial electrode 12. This illustration shows that the triaxial configuration is particularly sensitive to capacitive changes in the vicinity of the tip 5a of the liquid transfer needle 5 at which the detection resistor 50 is disposed for monitoring purposes.

Figure 9:
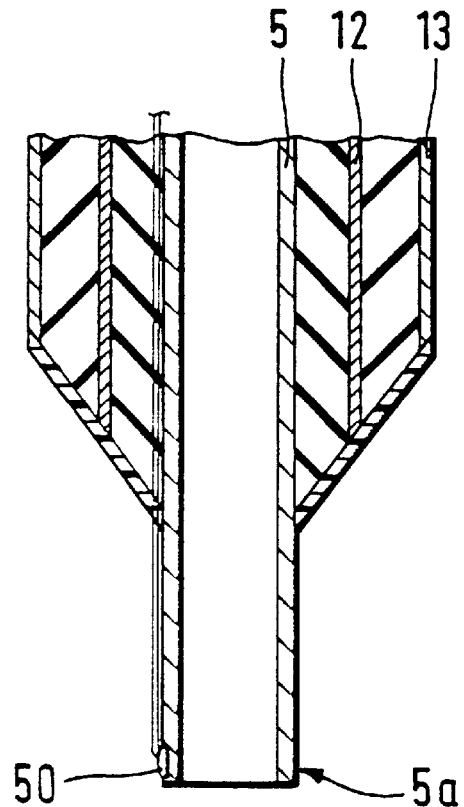
FIG. 9 shows a cut through the lower end of a liquid transfer needle.

FIG. 9 shows a cut through the lower end of a liquid transfer needle 5 having a detection resistor 50. The detection resistor 50 should be smooth, without protruding surfaces and should be properly mechanically mounted and electronically connected. It could also be provided with a liquid repellent nanocoating. One could, for example, utilize NTC or PTC resistor tabs with which structures of 0.1 to 0.2 mm in size can be obtained and which could be inserted into a depression or an opening in the vicinity of the tip of the needle 5a. The detection resistor 50 can be cast within a chemically resistive molding agent.

Figure 10:
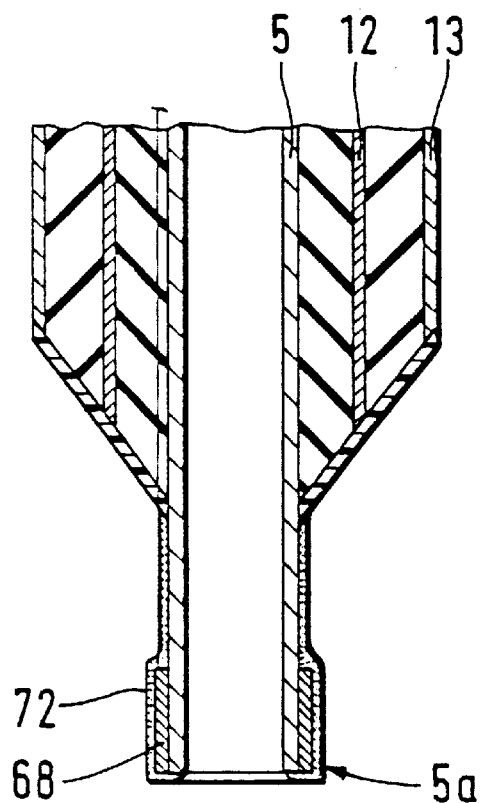
FIG. 10 shows a modification with respect to FIG. 9.

FIG. 10 shows an alternative configuration of a resistance film or a resistance foil 68 which is not affected by the respective liquid and which could be wound at the inside or outside of the liquid transfer needle 5. The resistance foil 68 is provided with a protective coating 72.

Figure 11:
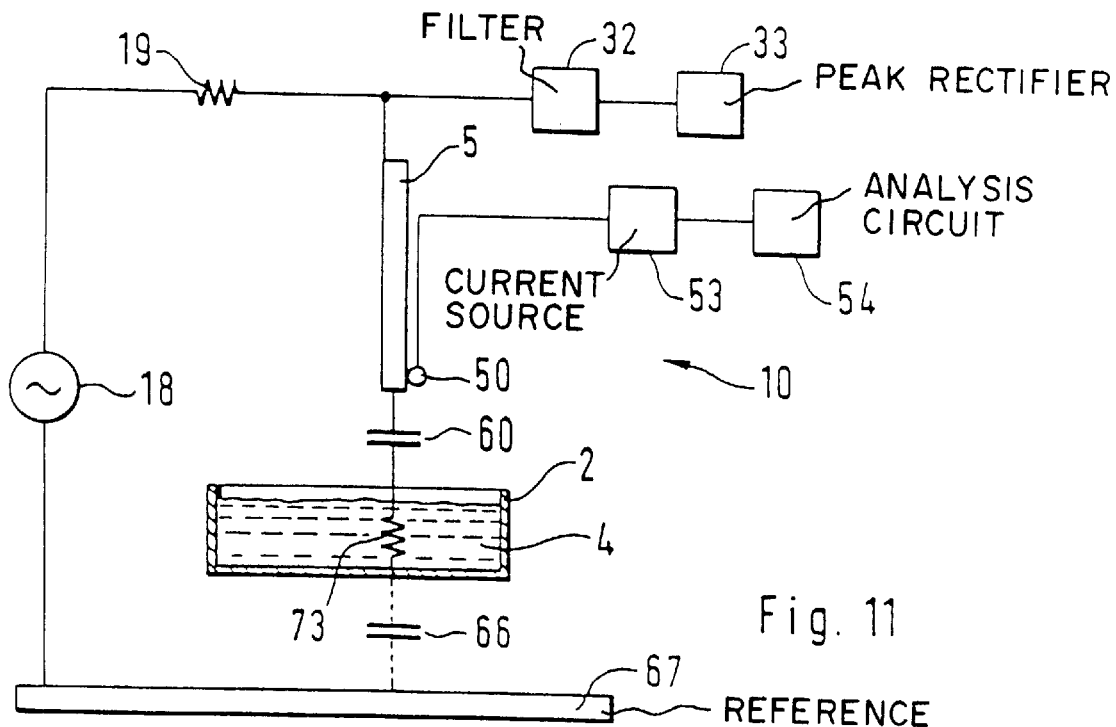
FIG. 11 shows a modification with respect to FIG. 8.

FIG. 11 shows a schematic representation of a modification of FIG. 8 in which a conventional capacitive liquid level detector 10 is provided, in accordance with the invention, with an additional detection resistor 50. In this measurement, the volume resistance 73 of the analysis liquid 4 is incorporated in the signal path. In this configuration, the measurement is more selective with respect to foam and bubble formation but more sensitive to stray influences and the influences of changes in separation.

Additional elements illustrated in the drawings include needle transport unit 6 with vertical column 7 movable upwards and downwards by a vertical drive (not shown), and swivel arm 8. Pivot circle 9 is defined by the pivoting or swivelling of swivel arm 8. Additionally, as shown in FIG. 3, coaxial electrode 12 has end 12a, and shield electrode 13 has end 13a. Dielectrics 14 and 15 are disposed as shown.

The above-discussed embodiment of the present invention is for illustrative purposes only. Numerous modifications can be made to this embodiment, while remaining within the spirit and scope of the invention. For a proper understanding of the metes and bounds of the present invention, reference should be made to the accompanying claims.

What is claimed is:

1. A liquid transfer device for an analysis unit, the liquid transfer device comprising:
   a liquid transfer needle having a tip; and
   a capacitive liquid level detector for detecting immersion of the tip of the liquid transfer needle into an analysis liquid by detecting a change in capacitance between a signal electrode and a counter electrode, the analysis liquid being contained in a vessel, said capacitive liquid level detector comprising a signal electrode, a counter electrode and a detection circuit connected to said signal electrode and said counter electrode for detecting a change in capacitance between the signal electrode and the counter electrode; and a temperature dependent detection resistor disposed adjacent the tip of the liquid transfer needle, wherein said tip of the liquid transfer needle and said temperature dependent detection resistor are movable into and out of the analysis liquid, wherein said detection circuit comprises a current supply for supplying current to the detection resistor, said detection circuit configured to detect a change in resistance of the detection resistor during immersion thereof into the analysis liquid.

2. A liquid transfer device according to claim 1, wherein the capacitive liquid level detector comprises a first coaxial electrode arrangement including said liquid transfer needle and a first coaxial electrode coaxially surrounding said liquid transfer needle, said first coaxial electrode being electrically insulated from said liquid transfer needle.

3. A liquid transfer device according to claim 2, wherein said first coaxial electrode arrangement including the liquid transfer needle and the first coaxial electrode coaxially surrounding said liquid transfer needle comprises a second coaxial electrode being electrically insulated from the liquid transfer needle and from the first coaxial electrode which second coaxial electrode surrounding the signal electrode functions as a shield electrode and a counter electrode and remains at a constant potential.

4. A liquid transfer device as recited in claim 2, wherein said detection circuit comprises an alternating voltage source and a voltage follower circuit, wherein an input to the follower circuit is connected to one of the signal and first coaxial electrodes; and wherein an output of the voltage follower circuit is connected to the another of the signal and first electrodes, in order to provide no voltage difference therebetween, the first electrode serving as a compensation electrode.

5. A liquid transfer device as recited in claim 4, wherein the signal electrode is connected to the input of the voltage follower circuit and the compensation electrode is connected to the output of the voltage follower circuit.

6. A liquid transfer device as recited in claim 4, wherein the signal electrode comprises the liquid transfer needle and is connected to the input of the voltage follower circuit, and wherein the compensation electrode comprises the first coaxial electrode, and is connected to the output of the voltage follower circuit.

7. A liquid transfer device as recited in claim 1, wherein said detection resistor comprises one of a resistance film and a foil.

8. A liquid transfer device as recited in claim 4, wherein at least a part of said detection resistor is disposed between said compensation electrode and said counter electrode.

9. A liquid transfer device as recited in claim 4, wherein at least one lead of said detection resistor is disposed between said compensation electrode and said counter electrode.

10. A liquid transfer device as recited in claim 3, wherein said detection resistor is connected between said signal electrode and said counter electrode.

11. A liquid transfer device as recited in claim 1, further comprising a processor connected to said detection circuit for processing output of the detection circuit, and a memory connected to said processor for storing data relating to behavior characteristics of the detection resistor.

12. A method for detecting immersion of a liquid transfer needle of an analysis apparatus liquid transfer device into an analysis liquid disposed in a vessel, said method comprising the steps of:

providing a liquid transfer device for an analysis unit, the liquid transfer device comprising a liquid transfer needle having a tip, a capacitive liquid level detector for detecting immersion of the tip of the liquid transfer needle into the analysis liquid, the analysis liquid being contained in a vessel, said capacitive liquid level detector comprising a signal electrode, a counter electrode and a detection circuit connected to said signal electrode and said counter electrode for detecting a change in capacitance between the signal electrode and the counter electrode, and a temperature dependent detection resistor disposed adjacent the tip of the liquid transfer needle, wherein said tip of the liquid transfer needle and said temperature dependent detection resistor are movable into and out of the analysis liquid, wherein said detection circuit comprises a current supply for supplying current to the detection resistor, said detection circuit configured to detect a change in resistance of the detection resistor during immersion thereof into the analysis liquid;

supplying current to the detection resistor;

detecting a change in capacitance between a signal electrode and a counter electrode;

detecting a change in resistance of the detection resistor upon immersion of the detection resistor and the tip of the liquid transfer needle into the analysis liquid.

13. A method according to claim 12, further comprising the steps of measuring an ambient temperature, and controlling the current flowing through the detection resistor to regulate the temperature of the detection resistor relative to the ambient temperature to a predetermined temperature difference.

14. A method according to claim 13, wherein said predetermined temperature difference is between 1 K and 10 K.

15. A method according to claim 13, wherein said predetermined temperature difference is between 3 K and 7 K.

16. A method according to claim 12, said method comprising a step of, prior to detecting the change in resistance of the detection resistor, lowering the liquid transfer needle into the analysis liquid in lowering step increments, with the lowering being continued after initial detection of contact with a surface of the liquid by the capacitive liquid level detector, said method comprising a further step of stopping the lowering after a plurality of sequential detections of liquid by the capacitive liquid level detector.

17. A method as recited in claim 16, wherein the step of detecting the change in temperature of the temperature dependent detection resistor is performed after the step of stopping the lowering motion, and comprising a further step of transferring liquid with the liquid transfer device, the transferring step being carried out after detection by the detection resistor that the needle is immersed in compact liquid, or after continuing the lowering step until it is detected that the detection resistor detects compact liquid.

18. A method as recited in claim 16, further comprising a step of transferring liquid with the liquid transfer device after stopping the lowering motion of the needle upon detection that the needle is immersed into the analysis fluid by the capacitive liquid level detector, while simultaneously measuring resistance of the detection resistor.

* * * * *